(12) United States Patent
Blasczyk et al.

(10) Patent No.: US 11,812,740 B2
(45) Date of Patent: Nov. 14, 2023

(54) METHOD FOR GENETICALLY MODIFYING A VASCULARISED TISSUE

(71) Applicant: MEDIZINISCHE HOCHSCHULE HANNOVER, Hannover (DE)

(72) Inventors: Rainer Blasczyk, Isernhagen (DE); Constanca Ferreira De Figueiredo, Neustadt am Rübenberge (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 907 days.

(21) Appl. No.: 16/615,085

(22) PCT Filed: May 23, 2018

(86) PCT No.: PCT/EP2018/063581
§ 371 (c)(1),
(2) Date: Nov. 19, 2019

(87) PCT Pub. No.: WO2018/215571
PCT Pub. Date: Nov. 29, 2018

(65) Prior Publication Data
US 2020/0170243 A1   Jun. 4, 2020

(30) Foreign Application Priority Data
May 26, 2017 (EP) .................................... 17173104

(51) Int. Cl.
*A01N 1/02* (2006.01)
*A61L 27/36* (2006.01)
*C12N 15/85* (2006.01)

(52) U.S. Cl.
CPC .......... *A01N 1/0226* (2013.01); *A01N 1/0284* (2013.01); *A61L 27/3625* (2013.01); *A61L 27/3687* (2013.01); *C12N 15/85* (2013.01)

(58) Field of Classification Search
None
See application file for complete search history.

(56) References Cited

U.S. PATENT DOCUMENTS

| | | | | |
|---|---|---|---|---|
| 5,908,624 | A * | 6/1999 | Scott | C12N 5/0641 435/177 |
| 8,236,771 | B2 | 8/2012 | Cicciarelli et al. | |
| 8,361,976 | B2 | 1/2013 | Kowalik et al. | |
| 2002/0127205 | A1 | 9/2002 | Edge | |
| 2010/0028848 | A1 | 2/2010 | Parker et al. | |
| 2011/0305772 | A1 | 12/2011 | Cameron | |
| 2014/0219970 | A1 | 8/2014 | Edinger et al. | |
| 2016/0017546 | A1 | 1/2016 | Straub et al. | |
| 2016/0157462 | A1 | 6/2016 | Taffler et al. | |

FOREIGN PATENT DOCUMENTS

| | | |
|---|---|---|
| WO | 2005108572 A1 | 11/2005 |
| WO | 2016057536 A1 | 4/2016 |
| WO | 2016196944 A1 | 8/2016 |

OTHER PUBLICATIONS

PFAU Andrea, International Search Report for Application No. PCT/EP2017/063581, dated Jul. 25, 2018.

* cited by examiner

*Primary Examiner* — Blaine Lankford
(74) *Attorney, Agent, or Firm* — Greer, Burns & Crain, Ltd.; Steven P. Fallon (57) ABSTRACT

The invention provides an ex-vivo method, i.e. an in vitro method, for genetically modifying cells of a vascularised tissue, which can be anorgan, during normothermic or subnormothermic perfusion without damaging the tissue or its cells due to oxygen undersupply. The method enables keeping the vascularised tissue at normothermic or subnormothermic conditions over a sufficient period of time to genetically modify the cells e.g. with viral vectors.

20 Claims, 3 Drawing Sheets

METHOD FOR GENETICALLY MODIFYING A VASCULARISED TISSUE

The present invention relates to an ex-vivo method, i.e. an in vitro method, for genetically modifying cells of a vascularised tissue, which can be an organ, during normothermic or subnormothermic perfusion without damaging the tissue or its cells due to oxygen undersupply. The method of this invention enables keeping the vascularised tissue at normothermic or subnormothermic conditions over a sufficient period of time to genetically modify the cells with viral vectors by supplying oxygen by oxygen carriers which are not red cells. The solid tissue is a vascularised tissue, preferably an organ such as the heart, the lung, the kidney, the pancreas, the upper or lower extremity or parts of it. The vascularised tissue can be for use as a transplant, e.g. in the treatment of a tissue defect. The genetic modification of the vascularized tissue can e.g. be the suppression of the expression of a protein, e.g. of MHC molecules or of dysfunctional molecules, the expression of a protein, and/or the modification of a gene. Methods for genetic modifications are generally known, e.g. transduction using genetically modified viral particles, and CRISPR/Cas9 modification methods.

In an allogeneic transplant setting the cells of a tissue or organ from a human donor for a human recipient can be modified such that the immunogenicity of the cells is reduced, minimized or abrogated. As a result, the immune system of the recipient does not recognize the tissue from the donor as foreign and will not initiate a host-versus-graft-reaction or an immunological rejection. The transplant is a solid tissue or organ originating from another individual, optionally of another species, preferably of the same species, e.g. an allogeneic transplant, preferably originating from another human and the recipient is a human, e.g. a human patient in need of a transplant. The vascularized tissue can be a homogeneic tissue, e.g. originate from the later recipient, and the genetic modification can be the introduction of a nucleic acid construct modifying the tissue, e.g. changing a mutation or genetic defect into a functional gene. The solid tissue transplant is vascularized and can e.g. be a part of an organ or an entire organ or an extremity or part of an extremity.

The method has the advantage of adapting the transplant prior to implantation into the recipient to the immune system of the recipient, which results in minimal or absence of an immune response by the recipient against the transplant. As a consequence, the method preferably allows providing a transplant which subsequent to the implantation into the recipient allows the presence of the transplant with drastically reduced administration of immunosuppressing agents, preferably without administration of immunosuppressing agents to the recipient.

For an allogenic transplant, this method has been applied to efficiently reduce the tissue's immunogenicity by integrating short hairpin RNAs (shRNAs) targeting MHC-related transcripts and thereby silencing MHC class I and class II expression. This procedure is likewise suitable to deliver transgenes that mediate a tolerogenic effect on immune cells, such as the gene for PD-L1, PD-L2, IDO, IL-10 and/or any other molecule or molecules that prevent activation or expansion of T cells or cytotoxic antibody effects as e.g. caused by complement factors, thereby reducing the immunogenicity of at least some cells of the tissue or organ, which can be an allogenic transplant, or in an autologous transplant setting reduce autoimmune responses against the genetically modified cells of the tissue, thereby at least mitigating the autoimmune disease, wherein the tissue or organ is autologous, to generate an autologous transplant. In an embodiment, in which the vascularized tissue is genetically modified to express PD-L1, PD-L2, IDO, IL-10 and/or any other molecule or molecules that prevent activation or expansion of T cells or cytotoxic antibody effects as e.g. caused by complement factors, the tissue can originate from the later recipient of the genetically modified tissue generated by the method, e.g. for use in the treatment of an autoimmune disease, as the expression of PD-L1, PD-L2, IDO, IL-10 and/or any other molecule or molecules that prevent activation or expansion of T cells or cytotoxic antibody effects as e.g. caused by complement factors reduces the immunogenicity of the tissue, and hence reduces the autoimmune response against the genetically modified cells of such tissue.

In addition, this procedure is likewise suitable to knock down or knock out genes whose proteins are targets of autoantibodies, thereby eliminating their targets and at least mitigating the autoimmune disease. The nucleic acid construct can comprise a transgene modifying the vascularized tissue, e.g. delivered by a viral vector, could also be the correct, i.e. natural functional gene for which the organ is carrying a gene defect, thereby correcting the gene defect of the organ, e.g. in Cystic Fibrosis by delivering the correct gene for the Cystic fibrosis transmembrane conductance regulator (CFTR). The nucleic acid construct can contain an expression cassette encoding proteins having the function of CRISPR/Cas, e.g. in combination with a transgene adapted for modifying a defect gene to the gene encoding a functional gene, for a genetic modification of the vascularised tissue.

STATE OF THE ART

U.S. Pat. No. 8,236,771 B2 describes a method for reducing the immunogenicity of a human allogeneic organ tissue by identifying HLA mismatches with the recipient and perfusing the tissue through its vasculature with a lentiviral vector which integrates and expresses siRNA directed against a consensus sequence among the mismatches in order to downregulate the expression of the mismatched HLA.

U.S. Pat. No. 8,361,976 B2 describes that perfusing a pancreas with an RNAi agent that downregulates a trait causing immunogenic rejection or ischemia-induced apoptosis prepares the pancreatic islets for transplantation.

WO 2005/108572 A1 describes sequences of siRNA molecules which are suitable for silencing the expression of HLA genes, which siRNA can e.g. be expressed from a lentiviral vector, in order to reduce immunogenic rejection of transplants. This demonstrated the feasibility to silence MHC expression in different types of cells and that MHC-silenced cells showed improved graft survival after allogeneic transplantation or transfusion.

US 2014/0219970 A1 describes the ex vivo perfusion of a placenta with PBS for isolating single cells, and the use of such isolated single cells for treatment of sarcoidosis.

WO 2016/057536 A1 describes the ex-vivo treatment of donor tissue by a protease or a glycosidase for reducing the presence of MHC prior to transplantation.

US 2016/0175462 A1 describes the genetic manipulation of an organism using the CRISPR/Cas system.

WO 2016/196944 A1 describes the ex vivo treatment of a transplant by activated protein C in a preservation solution, without genetic manipulation of the transplant.

US 2011/0305772 A2 describes introducing nucleic acids ex vivo into liver using slow low pressure infusion.

US 2010/0028848 A1 describes introducing nucleic acids, e.g. siRNA, ex vivo into a transplant organ for suppressing rejection reactions by perfusing or bathing the organ in a liquid containing the nucleic acids.

US 2002/0127205 A1 describes the genetic manipulation of single cells for use in transplantation.

OBJECT OF THE INVENTION

It is an object of the invention to provide a method to genetically modify cells of a vascularised tissue or organ by e.g. viral transduction during subnormothermic or normothermic perfusion, thereby avoiding cell or tissue damage due to oxygen undersupply.

In one embodiment, it is an object of the invention to provide an alternative method for modifying the expression of immunogenic protein in a transplant, especially for modifying the expression of HLA in a tissue forming a transplant in order to provide an efficient and permanent reduction of immunogenic protein in the transplant and to reduce the immunogenic response by the recipient against the transplant.

DESCRIPTION OF THE INVENTION

In contrast to the genetic modification of single cell cultures, monolayers or simple tissues which has become routine in gene therapy laboratories, so far the feasibility to permanently genetically engineer vascularized tissues or solid organs such as the heart, the lung, the kidney, the pancreas, of an upper or lower extremity remained virtually impossible due to major anatomical, structural and technical problems. In particular the organ endothelium, as a main target for adverse immune or thrombogenic responses, is an important candidate for genetic engineering. Although some experimental strategies have been performed to genetically manipulate hearts, those were based on the use of adenovirus-associated vectors (AAV) which remain episomal and thus only contribute for a transient expression of the transgene. However, for a stable therapeutic effect, the tissue's or organ's cells will need to be genetically modified in a permanent manner, which requires a stable expression of a transgene or regulatory molecule. Hence, the use of integrating vectors, such as lentiviral vectors would be desirable. However, the large endothelium area of a vascularized solid organ requires large amounts of lentiviral particles. In contrast to AAV, lentiviral vectors contribute to stable gene expression, but it is difficult to produce them at high concentrations sufficient to transduce the large organ's endothelium. Furthermore, lentiviral vectors are targeted by human complement and therefore lentiviral particle concentrations decrease fast after resuspension of the vector in blood. Also, the adherence of lentiviral particles to the blood cells makes an efficient transduction of the tissue's or organ's cells impossible.

The present invention establishes a method to genetically modify cells of a vascularized tissue by ex vivo perfusion under normothermic to subnormothermic conditions in the absence of blood, in particular in the absence of red cells and plasma proteins such as complement, without generating ischemic injuries due to oxygen undersupply. The genetic modification is exemplified by transduction via viral vectors. In the example the lung cells and in particular the endothelium cells were efficiently transduced with a lentiviral vector encoding for shRNAs to silence the expression of MHC class I and class II without ischemic damage of the tissue due to a sufficient oxygen supply in the absence of blood, e.g. red cells or complement inhibiting target cell transduction. This was achieved by the application of artificial oxygen carriers which ensure oxygen supply to the tissue without inhibiting the action of the shRNA delivering particles to the target cells which would otherwise occur by the use of blood or blood cells adsorbing the particle and thereby inhibiting the delivery of the nucleic acid to the target cells.

The method described here allows for the efficient transduction of the cells of a vascularized tissue or a solid organ by perfusing the tissue under normothermic or subnormothermic conditions for at least 12 hours with preservation solution containing the compounds for genetic modification, herein exemplified by a lentiviral vector. This strategy for the first time allows the genetic modification of a vascularized tissue, exemplified by the silencing of MHC class I and class II expression in the cells of a vascularized tissue or organ without compromising its structure or cell viability. The use of a genome integrating lentiviral vector allows for the permanent suppression of MHC expression. Silencing MHC expression in the tissue's or organ's cells in particular of the endothelium has the potential to abrogate harmful allogeneic immune responses and prevent transplant rejection.

This method has been established using the lung and the kidney as a model and is suitable for the genetic modification of other vascularized organs such as heart and pancreas, as well as upper or lower extremities or parts of it. This method represents a novel method to genetically modify vascularized tissues or organs and to reduce the immunogenicity of the vascularized tissue or the entire organ.

Generally preferred, perfusing the tissue via its vasculature includes perfusing any bronchia, ureter and/or intestine that are present in the vascularised tissue.

This method has been applied to efficiently reduce the tissue's immunogenicity by integrating short hairpin RNAs (shRNAs) targeting MHC-related transcripts and thereby silencing MHC class I and class II expression.

This method is likewise suitable to deliver short hairpin RNAs targeting transcripts of genes whose proteins are targets of autoantibodies and/or autoreactive immune cells, thereby eliminating their targets and at least mitigating the autoimmune disease.

This method facilitates genetic modification, e.g. the transduction, of the endothelium and/or other cells and therefore it optionally can be used not only for the expression of small shRNAs or microRNAs, but also for the expression of specific genes to induce a precise therapeutic effect. Such genes e.g. encode for the sequence of the Programmed Death-Ligand 1 (PD-L1), Programmed Death-Ligand 2 (PD-L2), Indolamin-2,3-Dioxygenase (IDO), Interleukin-10 (IL-10) and/or any other molecule or molecules that prevent activation or expansion of T cells or cytotoxic antibody effects as e.g. caused by complement factors, which are considered to play an active role in the prevention of alloreactive immune responses. PD-L1 and PD-L2 was demonstrated to play a critical role in the maintenance of peripheral tolerance. The engagement of these ligands with their receptor PD-1 trigger signalling pathways that prevent the activation of alloreactive T-cells and can induce the development of regulatory T cells. PD-L1 and PD-L2 has been speculated to play a major role in suppressing the immune system during particular events such as pregnancy, tissue allografts, autoimmune disease and other disease states such as hepatitis. Normally the immune system reacts to foreign antigens where there is some accumulation in the lymph nodes or spleen which triggers a proliferation of antigen-specific CD8+ T cells. The binding of PD-L1 or PD-L2 to PD-1 or B7.1 transmits an inhibitory signal which reduces the proliferation of these CD8+ T cells at the lymph nodes and supplementary to that PD-1 is also able to control the accumulation of foreign antigen specific T cells in the lymph nodes through apoptosis which is further mediated by a lower regulation of the gene Bcl-2. In addition, the tryptophan-depleting enzyme indoleamine-2,3-dioxygenase (IDO) and Interleukin-10 (IL-10) are critical for the regulation of immune tolerance. The method described herein preferably allows for the stable expression of such proteins on the organ's endothelium or other cells to induce and maintain a tolerogenic state towards the graft in combination or independently of other mechanisms of regulation of gene expression.

Thus, this method is likewise suitable to deliver transgenes that mediate a tolerogenic effect on immune cells, such as the gene for PD-L1, PD-L2, IDO or IL-10, thereby reducing the immunogenicity or alloimmune responses of at least some cells of the tissue or organ or reduce autoimmune responses against the genetically modified cells of the tissue, thereby at least mitigating the autoimmune disease or alloimmune rejection.

The transgene delivered by the viral vector could also be the correct gene for which the organ is carrying a gene defect, thereby correcting the gene defect of the organ, e.g. in Cystic Fibrosis by delivering the correct gene for the Cystic fibrosis transmembrane conductance regulator (CFTR).

The invention achieves the object especially by the features of the claims and provides a method for genetically modifying a vascularized tissue, e.g. for stable expression of a transgene, of a shRNA or for modifying a gene by genome editing technologies. In a transplant setting the invention provides a method for stably reducing the expression of immunogenic proteins, e.g. of matched or mismatched HLA molecules, in a vascularized allogeneic tissue forming a transplant, which method supplies oxygen to the cells of the tissue during the in vitro phase at normothermic or subnormothermic conditions in the absence of red cells and thus avoids ischemic injury. The method is ex vivo, i.e. in vitro, and comprises the steps of a) perfusing an isolated vascularized tissue with a preservation solution having a temperature of 2 to 10° C., preferably while incubating the isolated vascularized tissue at a temperature of 2 to 10° C., in order to generate a cooled isolated vascular tissue with reduced blood content and which tissue has a reduced metabolic activity, b) washing, e.g. by perfusing the vascularized tissue using the preservation solution or preferably a first perfusion solution, which preservation solution or respectively first perfusion solution preferably has a temperature of 2 to 10° C., until all red blood cells are removed from the vascularized tissue, preferably while incubating the isolated vascularized tissue at a temperature of 2 to 10° C., in order to generate a cooled isolated vascular tissue essentially free from blood and red cells and which tissue has a reduced metabolic activity, c) wherein optionally steps a) to b) are without introducing oxygen into the preservation solution or first perfusion solution, d) replacing the preservation solution or respectively the first perfusion solution with a second perfusion solution which contains at least one synthetic oxygen carrier which does not absorb or adsorb nucleic acid constructs, e.g. does not absorb viral vectors, e.g. by perfusing the vascularized tissue with the second perfusion solution, the second perfusion solution having a temperature of 2 to 38° C., preferably while incubating the isolated vascularized tissue at a temperature at 2 to 38° C., and e) introducing oxygen into the second perfusion solution, e.g. by connecting an oxygenator with the isolated vascularized tissue, and pumping the second perfusion solution containing oxygen through the isolated vascularized tissue, and temperature-adjusting the isolated vascularized tissue while perfusing the isolated vascularized tissue with the second perfusion solution, e.g. by application of a heating device, to a temperature of 20 to 38° C., preferably 34° C., in order to generate a subnormothermic or normothermic isolated vascular tissue having essentially no ischemic damage, which ischemic damage could e.g. be caused by lack of oxygen, f) introducing into the second perfusion solution a nucleic acid construct containing an expression cassette which encodes the sequence of interest, which e.g. in a transplant setting is at least one shRNA degrading or blocking by RNA interference the mRNA encoding for at least one MHC protein of the isolated vascularized tissue, g) continuing perfusing the isolated vascularized tissue with the second perfusion solution containing the introduced nucleic acid construct, at the temperature of 20 to 38° C., preferably 34° C., e.g. for at least 30 min, e.g. up to 12 h, and h) replacing the second perfusion solution containing the introduced nucleic acid construct with blood containing red cells and perfusing the isolated vascularized tissue with the blood at the temperature of 20 to 38° C., preferably 34° C., to provide optimal oxygen supply and to adsorb residual nucleic acid constructs thereby producing a genetically modified vascularized tissue free of unabsorbed circulating nucleic acid constructs, e.g. also enhancing safety for subsequent applications of the tissue, and i) replacing the blood with cold preservation solution having a temperature of 2 to 10° C., and perfusing the isolated vascularized tissue at a temperature of 2 to 10° C., preferably while incubating at 2 to 10° C. in order to generate a cooled isolated vascular tissue with reduced blood content and which tissue has a reduced metabolic activity, j) wherein optionally step i) is without introducing oxygen into the preservation solution, k) having then in a transplant setting generated a vascularised and safe tissue or organ with reduced immunogenicity and which is useable as a transplant for an allogeneic recipient, in this sequence of steps.

Generally, subnormothermic conditions can be a temperature of from 0° C. up to a temperature of 1K or 2K below the normal core body temperature of the organism from which the vascularized tissue originates, e.g. subnormothermic conditions can be from a temperature of up to 20K or up to 15 or up to 10K below the normal core body temperature of the organism from which the vascularized tissue originates up to 1K or 2K below this normal core body temperature. Normothermic conditions can be a temperature of 2K or 1K below the normal core body temperature of the organism from which the vascularized tissue originates up to a temperature of 2K, preferably 1K higher than the normal core body temperature of the organism from which the vascularized tissue originates, or up to the normal core body temperature of the organism from which the vascularized tissue originates.

Generally preferred, the method is carried out in an organ perfusion system having a device for cooling and heating and at a temperature in the range of subnormothermic conditions to normothermic conditions. For human, subnormothermic conditions are 20 to 36° C. and normothermic conditions are 36° C. to 38° C.

Preferably, the isolated vascularized tissue is continuously perfused during the entire method.

The preservation solution and the first perfusion solution can have the same composition and preferably comprise or consist of Potassium phosphate, Potassium lactobionate, Magnesium sulphate, hydroxyethyl starch, Raffinose, Adenosine, Glutathione and Allopurinol (HTK, UW, Cortosol, Eurocollins Solutions, as for the kidney and liver) in an aqueous composition, or as an alternative the preservation solution or first perfusion solution can be a Low-Potassium-Dextran solution including Sodium chloride, Potassium chloride, Dextran, Magnesium, Glucose, Phosphate and Chloride in an aqueous composition (OCS Solution, Perfadex, Steen Solution, as for the lung).

The second perfusion solution preferably comprises of or consists of the first perfusion solution and at least one oxygen carrier, preferably a Haemoglobin-based oxygen carrier (HBOX).

The at least one synthetic oxygen carrier contained in the second perfusion solution, is preferably dissolved or dispersed. The at least one synthetic oxygen carrier is e.g. selected from the group comprising or consisting of synthetic or isolated haemoglobin, optionally polymerized resulting in microparticles in the range of 350 to 700 nm such as Hbmp-700, perfluorocarbon compounds, e.g. perfluorodecalin or dodecafluoropentane, and/or mixtures of at least two of these.

Optionally, the first perfusion solution contains at least one synthetic oxygen carrier. Further optionally, the first perfusion solution and the second perfusion solution have the same composition.

Optionally, steps c), d) and e) can be combined such that the nucleic acid construct is contained in the second perfusion solution when replacing the first perfusion solution with the second perfusion solution.

Optionally, the second perfusion solution contains protamine sulphate, e.g. at 8 mg/L, 10 000 IC heparin and/or 500 mg/L methylprednisolone (e.g. available under the designation Urbason).

Generally, the compositions of the preservation solution (first perfusion solution) and/or the second perfusion solution are adjusted to induce a reduced metabolic activity in the vascularized tissue. This adjustment can e.g. be achieved by these solutions being free from carbohydrates and/or contain less than 0.05 mM Glucose.

The nucleic acid construct containing an expression cassette encodes for a transplant setting a transcript for inactivating the mRNA that encodes the MHC of the isolated vascularized tissue in order to reduce the immunogenicity of the isolated vascularized tissue towards the immune system of the recipient. The transcript for inactivating the mRNA encoding the MHC can be a transcript known in prior art or a transcript hybridizing to the known mRNA encoding the MHC of the isolated vascularized tissue. For example, the transcript can be a RNA specific for β2-microglobulin mRNA and/or for the mRNA encoding MHC class II transactivator, e.g. in the form of shRNA. The transcript can e.g. be in the form of a shRNA (small hairpin RNA), siRNA (small interference RNA), or microRNA. The expression of such transcripts leads to a downregulation of MHC class I and/or of MHC class II expression by RNA interference, thereby reducing immunogenicity of the vascularized tissue for a recipient. The expression cassette can be contained in a viral vector, which preferably is packaged in a viral particle, e.g. as a lentiviral vector packaged in lentiviral particles.

The blood used in step h) can be whole blood, optionally diluted with a medium supporting tissue viability, e.g. a synthetic medium composition as the perfusion solution, or it can be packed red cells, optionally diluted in plasma or 0.9% Sodium Chloride solution or PBS or perfusion solution or any other physiological diluent not affecting red cell function and being compatible with the tissue to be perfused.

In a transplant setting, it was found that this method results in the ex vivo generation of a transplant which has very little ischemic damage, e.g. very little or no damage caused by lack of oxygen, wherein the vascularized allogeneic tissue in addition is effectively genetically modified such that its original MHC molecules are present at a reduced level and preferably its original MHC molecules are substantially reduced in their expression, e.g. the MHC molecules are expressed at a reduced level or are absent.

The vascularized tissue produced according to this method is for use as a transplant in the treatment of a failing vascularized tissue, e.g. by replacing at least partially a homologous vascularized tissue in a recipient, wherein the vascularized tissue originally was allogeneic to the recipient.

The method has the advantage of generating a vascularized tissue which is isolated, e.g. present in vitro, and having essentially no ischemic damage, which ischemic damage is e.g. determined as the content of apoptotic cells, the existence of oedemas, the expression or secretion of injury markers such as endothelin-1, IL-6, KLF-2, eNOS, etc.

The MHC molecules, in human tissue also termed HLA molecules, preferably comprise both class I and class II molecules.

Optionally, the method in step e) may comprise introducing into the vascularized tissue a nucleic acid construct, which comprises an expression cassette encoding a tagging molecule. The nucleic acid construct comprising an expression cassette encoding a tagging molecule may be the only nucleic acid construct, or the nucleic acid construct comprising an expression cassette encoding a tagging molecule is an additional nucleic acid construct to be introduced in the method, e.g. in step e).

The tagging molecule is usually functionally inactive and can e.g. be a truncated natural receptor, e.g. delta-NGFR (dNGFR), truncated-CD34 (tCD34) or a fetal protein, e.g. al-fetus protein, or an artificial amino acid sequence.

The promoter of the expression cassette encoding the tagging molecule may be a promoter which is inducible by an external stimulus, e.g. a tetracycline-inducible promoter, a CMV promoter, or a promoter that is constitutively active in endothelial cells, e.g. the eNOS-promoter.

The expression of a tagging molecule allows compounds having preferentially selective affinity for the tagging molecule to specifically target the vascularized tissue in vivo, especially its endothelial cells. Accordingly, expression of a tagging molecule allows compounds having selective affinity for the tagging molecule for use in the selective treatment of the implanted tissue, e.g. for adsorption of compounds having affinity preferentially for the tagging molecule to the vascularized tissue, or for uptake of compounds having affinity for the tagging molecule by the vascularized tissue, which is obtainable by the method of the invention. Compounds having affinity for a tagging molecule may e.g. be a binding peptide, e.g. an antibody having a natural structure, e.g. an IgG, or an artificial structure, e.g. an scFv or a Fab fragment, or the binding ligand or modified binding ligand in case of the tagging molecule being a truncated receptor, e.g. neurotrophins or functionally inactive variants thereof in the case of dNGFR.

Accordingly, this embodiment provides a vascularized tissue which constitutively or inducibly expresses a tagging molecule, e.g. on endothelial cells of the vascularized tissue, and allows the treatment of this vascularized tissue by in vivo targeting when implanted into a recipient, by administration of a compound having affinity for the tagging molecule. This embodiment has the advantage of providing a vascularized tissue implant which can specifically be targeted in vivo by compounds having affinity for the tagging molecule, e.g. in systemic administration of a compound having affinity for the tagging molecule. Generally, the compound having affinity for the tagging molecule can be coupled to an effector compound or be present in admixture with an effector compound, wherein the effector compound can be provided for use in the treatment of the vascularized tissue implant.

The method is now described in greater details by way of an example and with reference to the figures, which show in FIG. 1 schematically steps of the method and previous step of explantation of the isolated vascularized tissue and the subsequent step of implantation of the isolated vascularized tissue, FIG. 2 results of measurements of expression of a reporter gene that was co-transduced into exemplary isolated vascularized tissue, FIG. 3 results of PCR analyses for the presence of the nucleic acid construct within exemplary isolated vascularized tissue resulting from the method, and in FIG. 4 relative expression levels of β2-microglobulin and MHC class II in exemplary isolated vascularized tissue resulting from the method.

Figure 1:
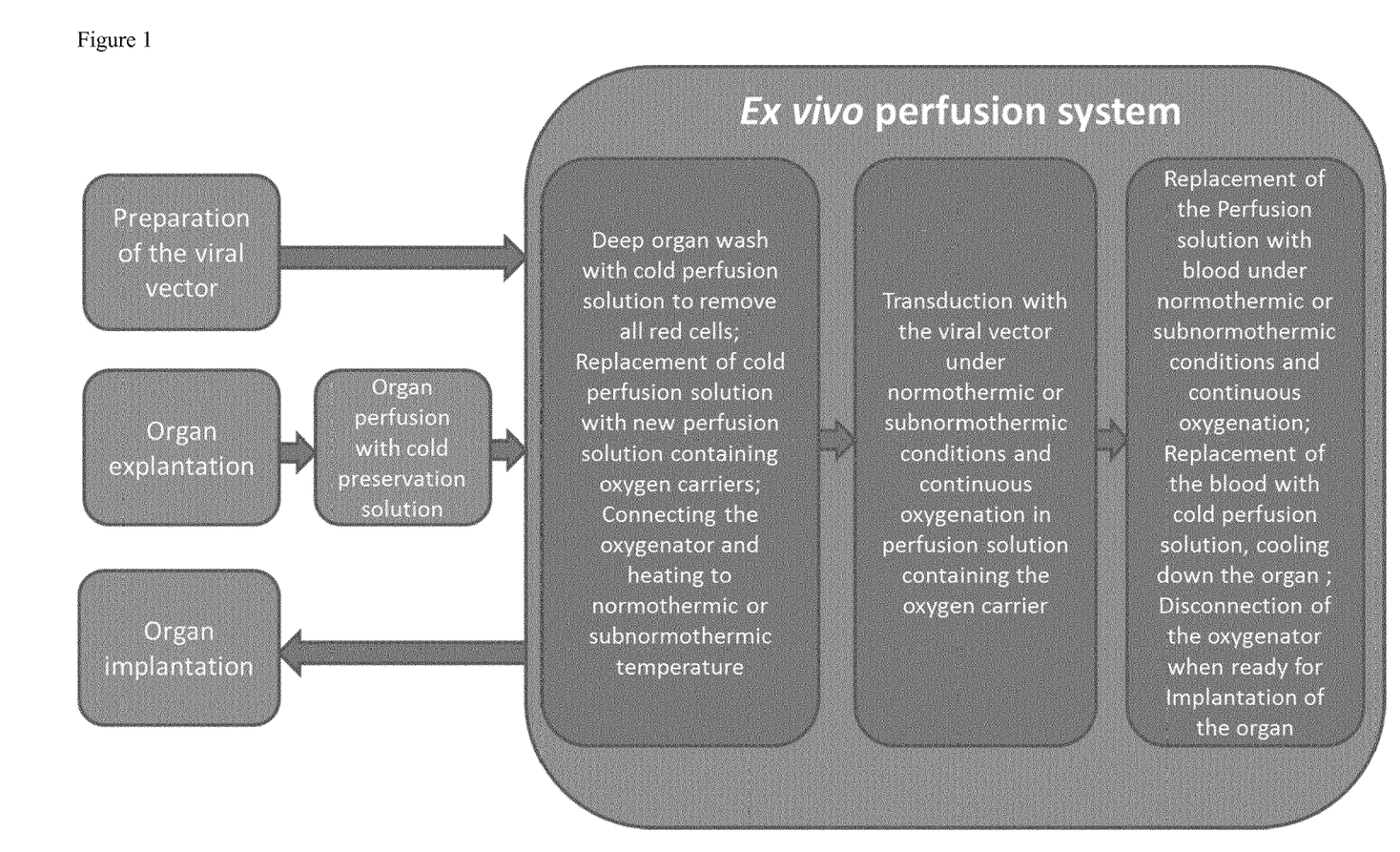

FIG. 1 schematically depicts a preferred method, starting with the perfusion of vascularized explanted tissue, represented by an organ, with the preservation solution, to provide the vascularized tissue suitable for implantation into an allogeneic recipient.

Example 1: Preparation of an Explanted Allogeneic Lung for Transplantation

As an example for an allogeneic isolated vascularized tissue, the explanted lungs (left and right) of two domestic pigs (30-33 kg) were used, which tissue was flushed with preservation solution (composed of Perfadex) having a temperature of 4° C. immediately after explantation. The flushed lungs of one pig were incubated and perfused using an ex vivo perfusion system (self-constructed and an Organ Care System from TransMedics, Inc.) with first perfusion solution composed of Perfadex for complete removal of red blood cells. During this step, the oxygenator was not connected to the perfusion system in order to prevent the accumulation of red blood cells in the membrane of the oxygenator, as the red blood cells are regarded as resulting in later absorption and loss of the lentiviral vector particles containing the nucleic acid construct. Following this extensive washing, the first perfusion solution was completely replaced with a second perfusion solution (composed of Perfadex or OCS Solution) and containing haemoglobin microparticles (Hbmp-700) as the synthetic oxygen carrier, and the perfusion was continued with the oxygenator connected in order to ensure oxygen supply to the tissue, the temperature was by applying a heating device continuously increased and maintained at 37° C. The perfusion was made with a flow of 0.7 L/min.

The nucleic acid construct encoded expression cassettes for an shRNA encoding SEQ ID NO: 1, which is specifically targeting the β2-microglobulin mRNA, and an shRNA encoding SEQ ID NO: 2, specifically targeting the MHC class II transactivator (CIITA), as well as the coding sequence for a secreted form of luciferase (NanoLuc, obtained from Promega, a secreted form of Oplophorus gracilirostris-derived luciferase) as a reporter gene. The shRNA targeting the β2-microglobulin mRNA causes silencing of MHC class I and the shRNA targeting the MHC class II transactivator (CIITA) causes silencing of MHC class II in a specific and selective manner.

This nucleic acid construct was packaged in lentiviral particles in packaging cells and concentrated by centrifugation at 35 000 rpm for 8 h and resuspended in the preservation solution. The titer was determined using p24 ELISA, storage was at −80° C.

Prior to addition of the viral particles to the second perfusion solution, protamine sulphate was added to a concentration of 8 mg/L, 10 000 IE heparin and 500 mg Urbason were added to the circulating second perfusion solution (total volume approximately 1.5 L), and the temperature of the second perfusion solution was raised to 34° C.

The lentiviral particles were added to $10^{11}$ viral particles/L of second perfusion solution, and perfusion was continued at 34° C. for 8 h. Afterwards, the second perfusion solution to which the viral particles were added was replaced by 1 L heparinized peripheral whole blood admixed with 500 mL Steen solution containing Dextran 40, human serum albumin and electrolytes, obtained from XVIVO Perfusion. The tissue was subsequently maintained in the perfusion system for up to 12 h.

For analyses, lung tissue was taken from different regions and digested with collagenase VI and dispase (both obtained from Sigma). At 96 h after the addition of the lentiviral vector to the second perfusion solution, endothelial cells of the lung macrovasculature and microvasculature were isolated after labelling with anti-CD31 using paramagnetic beads (Dynabeads, obtained from Thermo Fisher) for magnetic separation. In parallel, endothelial cells were isolated from a non-transduced lung which was treated in the same way, except that no viral particle was added. Analyses showed that endothelial cells were isolated at purities above 70%.

At 24 h after addition of the viral particles to the second perfusion solution, luciferase activity was detected in the culture supernatant. The levels of this bioluminescence increased during the 96 h of cultivation. Remarkably, cells from both the right and the left lung showed to be transduced, indicating integration and activity of the nucleic acid construct in the entire organ epithelium. Luciferase activity was measured after addition of luciferase substrate (Furimazine, Promega).

Figure 2:
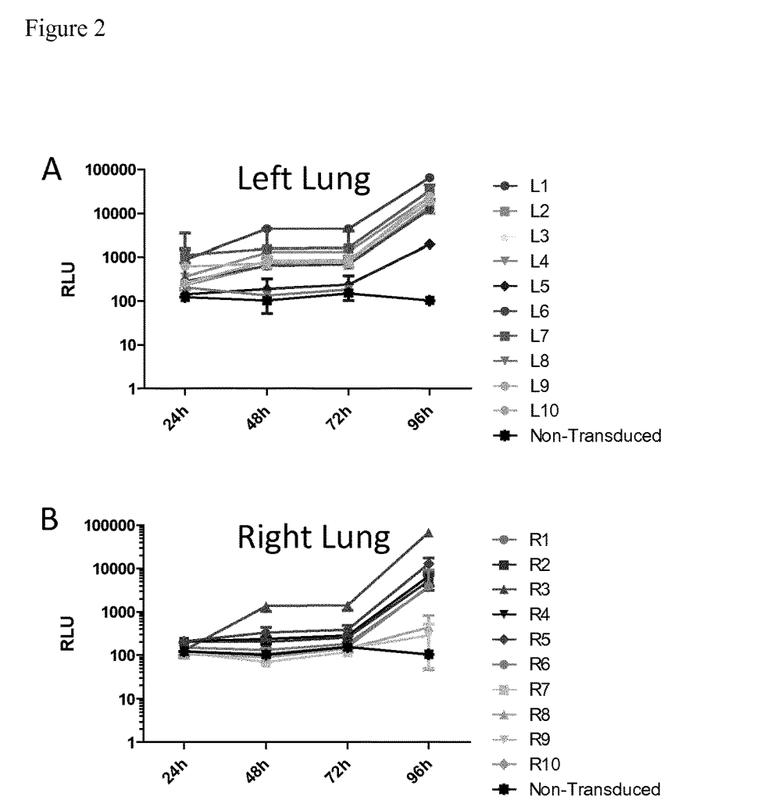

FIG. 2 shows the luminescence of the reporter gene for different regions of the left lung (samples L1 to L10) and for different regions of the right lung (samples R1 to R10) during the cultivation, as well as a parallel negative cell sample from the non-transduced lung (Non-Transduced).

The lentiviral particles provided for stable and permanent integration of the expression cassettes from the nucleic acid construct into the genome of the vascularized tissue.

Figure 3:
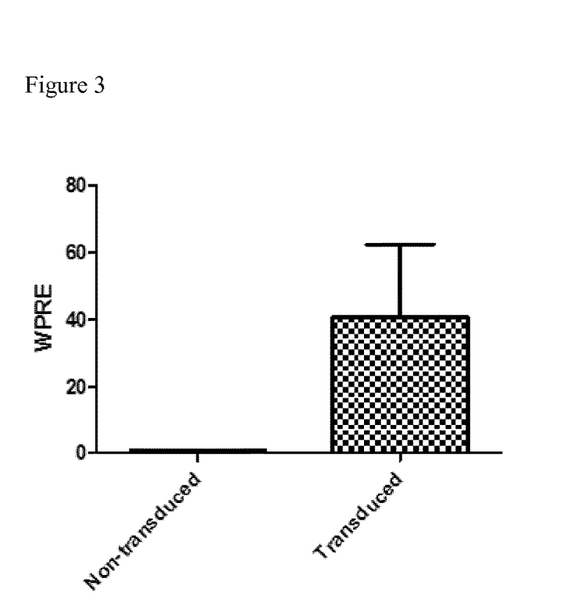

FIG. 3 shows the results of real-time PCR using DNA that was isolated from the cultivated endothelial cells and primers that were specific for the woodchuck hepatitis virus posttranscriptional element WPRE, which is present in the nucleic acid construct. The result shows the high levels of WPRE in the endothelial cells treated by the method of the invention, and background levels in the endothelial cells from the lung that were treated in parallel but without addition of the lentiviral vector.

Isolated cells were cultured in EBM-2 endothelial cell growth medium (obtained from Lonza). Endothelial cells were stimulated with IFN-γ (100 ng/mL) for 48 h. It was found that endothelial cells from the microvasculature of the non-transduced parallel treatment were able to upregulate β2-microglobulin and SLA-DR transcript levels ($p<0.001$) upon exposure to IFN-γ, but microvascular endothelial cells from the lungs treated with the nucleic acid construct according to the invention, contained in the lentiviral particle, did not show increased β2-microglobulin and SLA-DR transcript levels upon IFN-γ stimulation.

These results demonstrate that the method of the invention effectively silences expression of MHC class I and of MHC class II in the vascularized tissue, without ischemic damage which could be caused by undersupply with oxygen.

Figure 4:
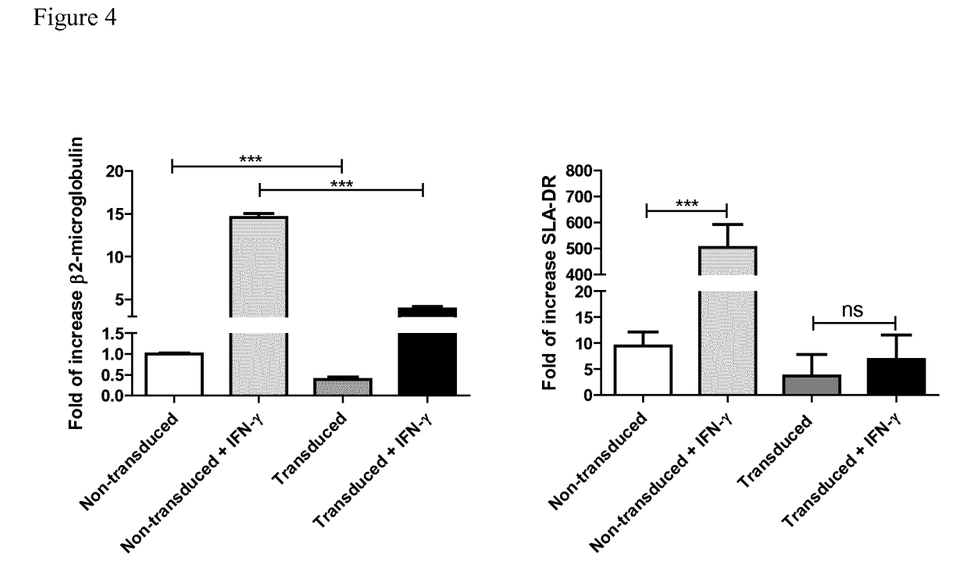

FIG. 4 shows the levels detected by RT-PCR for transcripts of β2-microglobulin and for transcripts of MHC class II (SLA-DR) after stimulation with IFNγ for 48 h in cultivated cells. Levels are normalized to levels of transcripts for β-actin (***$p<0.001$).

Example 2: Use of an Explanted Allogeneic Lung as a Lung Transplant

As an example for an allogeneic vascularized tissue, the left lung prepared by the method steps of Example 1 from explanted lungs of male miniature swines was used as a transplant for the left lungs of female miniature pigs.

In detail, the female recipient miniature swines were sedated and orotracheally intubated. Isoflurane was administered for anesthesia. A permanent vascular access double-lumen 3.2 Quinton atrial catheter was inserted into the right jugular vein. After thoracotomy in the fourth intercostal space the left lung hilus was dissected, the vessels and bronchus clamped and the lung was removed. The genetically modified (MHC silenced) or unmodified control donor lungs, respectively, was meanwhile cooled in the ex vivo perfusion system. The lung was removed from the ex vivo perfusion system, flushed with fresh cold perfusion solution and prepared for implant. The left lung was then transplanted using standard techniques. After extubation, the animals were put in boxes provided with heating lamps, underfloor heating and drinking water. All transplanted animals received standard intravenous pharmacologic immunosuppression for 28 days. Intravenous pharmacologic immunosuppression includes 1.5 mg/kg/d methylprednisolone and tacrolimus (Astellas, Japan) adjusted to blood trough levels of 16-26 ng/ml. Tacrolimus blood trough levels were monitored using tandem mass spectrometry. Empiric intravenous antibiotic therapy consisted of 4 mg/kg/d Ciprofloxacin (Bayer, Germany). After 28 days, the treatment with medicaments was discontinued; the Quinton catheter explanted and the animals were regularly controlled for signs of rejection by chest radiographs, and bronchoscopies. The expression of the lentiviral vector-encoded sequences was monitored by measuring the secreted luciferase (Nano-Luc) activity in the peripheral blood of the pigs in regular time intervals. Monitoring the expression of the reporter gene allows the indirect follow up of the MHC silencing effect in the graft without requiring an invasive procedure.

Animals that were transplanted with a genetically modified organ to silence MHC expression did neither show clinical nor radiological signs of immunological organ rejection within an observation period of 270 days, whereas animals that were transplanted with an unmodified lung rejected the graft at the latest 70 days after transplantation.

The invention claimed is:

1. A method for ex vivo genetically modifying a vascularized tissue, comprising at normothermic or subnormothermic conditions the steps of
    a) perfusing the vascularized tissue with a preservation solution having a temperature of 2 to 10° C.,
    b) washing by perfusing the vascularized tissue using the preservation solution or a first perfusion solution, until all red blood cells are removed from the vascularized tissue in order to generate a cooled isolated vascular tissue essentially free from blood and which tissue has a reduced metabolic activity,
    c) replacing the preservation solution or the first perfusion solution with a second perfusion solution which contains at least one synthetic oxygen carrier, and
    d) introducing oxygen into the second perfusion solution in order to generate a cooled isolated vascular tissue having essentially no ischemic damage,
    e) introducing into the second perfusion solution a nucleic acid construct,
    f) continuing perfusing the isolated vascularized tissue with the second perfusion solution containing the introduced nucleic acid construct, at the temperature of 20 to 38° C., wherein the solutions are free from blood cells, and
    g) replacing the second perfusion solution containing the introduced nucleic acid construct with blood and perfusing the isolated vascularized tissue with the blood to produce a vascularized tissue which is genetically modified by the nucleic acid construct.

2. The method according to claim 1, wherein the preservation solution and the first perfusion solution have the same composition.

3. The method according to claim 1, wherein the preservation solution, the first perfusion solution and/or the second perfusion solution are adjusted to effect a reduced metabolic activity in the vascularized tissue.

4. The method according to claim 1, wherein steps a) to c) are conducted without introducing oxygen into the preservation solution or first perfusion solution.

5. The method according to claim 1, wherein step f) is conducted at 20 to 38° C. for at least 30 min, preferably for at least 8 h.

6. The method according to claim 1, wherein perfusing is by connecting a pump with at least one of the blood vessels of the isolated vascularized tissue and pumping the solution through the at least one of the blood vessels.

7. The method according to claim 1, wherein the vascularized tissue is an organ selected from the group consisting of a heart, kidney, liver, lung, pancreas, small intestine, or a complete or partial extremity.

8. The method according to claim 1, wherein the vascularized tissue is allogeneic in respect of an intended recipient and that the nucleic acid construct encodes a transcript inactivating the mRNA encoding the MHC of the isolated vascularized tissue.

9. The method according to claim 1, wherein the vascularized tissue is autologous in respect of an intended recipient.

10. The method according to claim 1, wherein the vascularized tissue is of human origin and the nucleic acid construct encodes a short hairpin RNA (shRNA) which is specific for conserved or polymorphic regions of transcripts of the tissue for MHC class I light chain (β2-microglobulin) and/or for transcripts for the MHC class I heavy chains and/or for transcripts of the MHC Class II Transactivator or MHC class II α-chains or β-chains, and/or the nucleic acid construct encodes PD-L1, PD-L2, IDO, IL-10 and/or any other molecule or molecules that prevent activation or expansion of T cells or cytotoxic antibody effects, and/or the nucleic acid construct encodes a transcript inactivating transcripts encoding an autoantigen of the vascularized tissue, and/or the vascularized tissue is lacking a functional gene.

11. The method according to claim 1, wherein the vascularized tissue is perfused via its arterial vasculature and non-vasculature conducts such as bronchia, ureter and/or intestine.

12. The method according to claim 1, wherein the nucleic acid construct is suitable for permanent modification of the genome of the cells of the vascularized tissue and/or suitable for permanent integration into the genome of the cells of the vascularized tissue.

13. The method according to claim 1, wherein the vascularized tissue is of human origin.

14. The method according to claim 1, wherein the vascularized tissue is immunologically compatible with the intended recipient.

15. The method according to claim 1, wherein the nucleic acid construct encodes proteins having the function of CRISPR/Cas.

16. The method according to claim 1, wherein the nucleic acid construct contains or consists of an expression cassette encoding a tagging molecule.

17. The method according to claim 1, wherein an additional nucleic acid construct is introduced in step e), which additional nucleic acid construct contains an expression cassette encoding a tagging molecule.

18. The method according to claim 16, wherein the tagging molecule is located on the cell surface and is functionally inactive.

19. The method according to claim 16, wherein the tagging molecule is selected from the group consisting of truncated cell-surface receptors and fetal proteins.

20. The method according claim 1, wherein the expression cassette encoding a tagging molecule comprises a promoter functionally linked to the sequence encoding the tagging molecule, which promoter is inducible by an external stimulus or is constitutively active in endothelial cells.

* * * * *